United States Patent
Kerschbaumer et al.

(10) Patent No.: US 9,522,222 B2
(45) Date of Patent: Dec. 20, 2016

(54) APPLICATION ARRANGEMENT WITH A MEDICINAL SUBSTANCE FLUID

(71) Applicant: Fresenius Kabi Austria GmbH, Graz (AT)

(72) Inventors: Andreas Kerschbaumer, Tirol (AT); Roland Gorges, Graz (AT); Patricia Grigoleit, Wiesbaden (DE); Christian Krenn, Pernegg (AT); Johann Schloegl, Wilhering (AT)

(73) Assignee: Fresenius Kabi Austria GmbH, Graz (AT)

(*) Notice: Subject to any disclaimer, the term of this patent is extended or adjusted under 35 U.S.C. 154(b) by 0 days.

(21) Appl. No.: 14/433,166

(22) PCT Filed: Oct. 2, 2013

(86) PCT No.: PCT/EP2013/070570
§ 371 (c)(1),
(2) Date: Apr. 2, 2015

(87) PCT Pub. No.: WO2014/053560
PCT Pub. Date: Apr. 10, 2014

(65) Prior Publication Data
US 2015/0273133 A1 Oct. 1, 2015

Related U.S. Application Data

(60) Provisional application No. 61/709,657, filed on Oct. 4, 2012.

(30) Foreign Application Priority Data

Oct. 4, 2012 (EP) ..................... 12187273

(51) Int. Cl.
*B65D 83/10* (2006.01)
*A61M 5/00* (2006.01)
(Continued)

(52) U.S. Cl.
CPC .......... *A61M 5/002* (2013.01); *A61M 5/31511* (2013.01); *B65B 3/003* (2013.01);
(Continued)

(58) Field of Classification Search
CPC .......... A61F 2/00; A61F 25/002; A61F 5/002; B65D 81/2069; B65D 81/24; B65D 81/266
(Continued)

(56) References Cited

U.S. PATENT DOCUMENTS 1,980,141 A * 11/1934 MacGregor ............ A45C 13/02
206/229
5,156,267 A * 10/1992 Yates, Jr. ............. B65D 43/162
206/364
(Continued)

FOREIGN PATENT DOCUMENTS

DE 10036832 12/2001
EP 1818069 8/2007
(Continued)

*Primary Examiner* — Jacob K Ackun
*Assistant Examiner* — Rafael Ortiz
(74) *Attorney, Agent, or Firm* — Occhiuti & Rohlicek LLP

(57) ABSTRACT

An application arrangement for a medicinal substance fluid includes an application syringe with a plastic container, wherein the plastic container is filled with an oxygen-sensitive medicinal substance fluid and an oxygen-tight cover which surrounds the application syringe in oxygen-tight manner.

16 Claims, 3 Drawing Sheets

Figure 1:
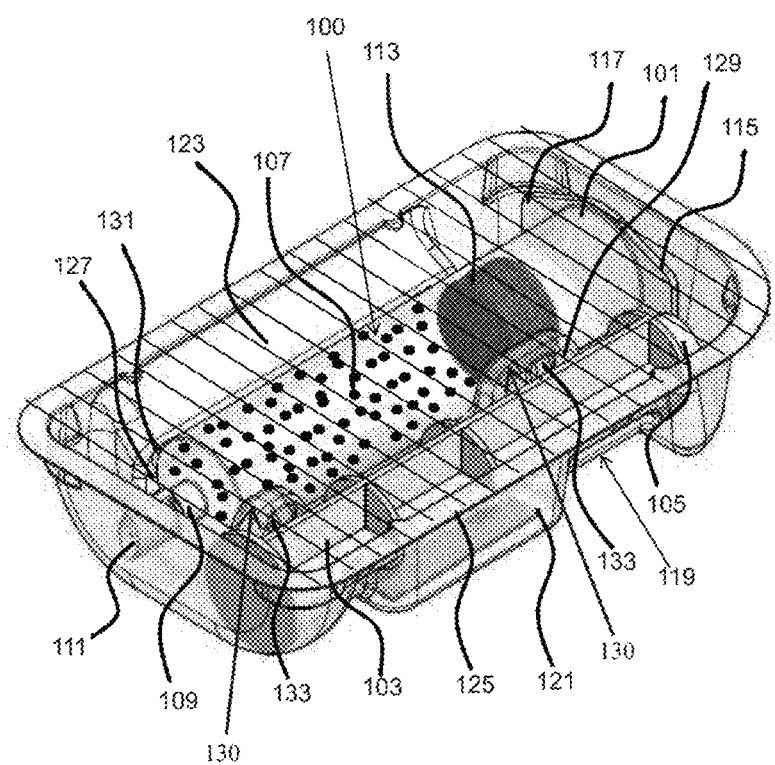

(51) Int. Cl.
*B65D 81/20* (2006.01)
*B65D 81/24* (2006.01)
*B65D 81/26* (2006.01)
*A61M 5/315* (2006.01)
*B65B 3/00* (2006.01)
*B65B 5/04* (2006.01)
*B65B 7/02* (2006.01)
*A61M 5/31* (2006.01)

(52) U.S. Cl.
CPC ............... *B65B 5/045* (2013.01); *B65B 7/02* (2013.01); *B65D 81/2069* (2013.01); *B65D 81/24* (2013.01); *B65D 81/266* (2013.01); *A61M 2005/3131* (2013.01); *A61M 2207/00* (2013.01); *A61M 2209/045* (2013.01)

(58) Field of Classification Search
USPC . 206/223, 570, 571, 363–365, 438; 424/424
See application file for complete search history.

(56) References Cited

U.S. PATENT DOCUMENTS

| | | | | |
|---|---|---|---|---|
| 2005/0009731 | A1* | 1/2005 | Desai | A61J 1/1412 |
| | | | | 435/6.13 |
| 2006/0118433 | A1* | 6/2006 | Nishio | A61J 1/2093 |
| | | | | 206/213.1 |
| 2006/0275336 | A1* | 12/2006 | Du Plessis | A61L 2/0011 |
| | | | | 424/423 |
| 2012/0143144 | A1* | 6/2012 | Young | A61M 5/283 |
| | | | | 604/195 |
| 2012/0277686 | A1* | 11/2012 | Muramatsu | A61M 5/3129 |
| | | | | 604/222 |

FOREIGN PATENT DOCUMENTS

| | | |
|---|---|---|
| EP | 2371406 | 10/2011 |
| EP | 2495002 | 9/2012 |
| JP | 2008-067989 | 3/2008 |

* cited by examiner

APPLICATION ARRANGEMENT WITH A MEDICINAL SUBSTANCE FLUID

CROSS REFERENCE TO RELATED APPLICATIONS

This application is a National Stage of International Application No. PCT/EP2013/070570 filed on Oct. 2, 2013, which claims priority to European Application No. 12187273.3 filed on Oct. 4, 2012 and U.S. Provisional Application No. 61/709,657 filed on Oct. 4, 2012, the contents of which are hereby incorporated by reference in their entirety.

The present invention relates to the field of administering active pharmaceutical ingredients.

The administration of active pharmaceutical ingredients typically involves using delivery syringes operable either by hand or by using a pump system. Conventional delivery syringes comprise a receptacle fillable with an active pharmaceutical ingredient, and also a plunger stored in a shiftable manner in the receptacle for the administration of the active pharmaceutical ingredient.

Active pharmaceutical ingredients administrable using a delivery syringe can be in the form of an active pharmaceutical ingredient emulsion fillable into a receptacle of a delivery syringe. In the case of oxygen-sensitive active pharmaceutical ingredients such as propofol, said active pharmaceutical ingredient emulsions are therefore typically stored in glass containers, such as glass bottles or vials for example. Thus, the active pharmaceutical ingredient can be stored in an oxygen-tight manner just before use and, when needed, transferred to a delivery syringe comprising a receptacle and then administered. However, such storage of active pharmaceutical ingredients is elaborate and therefore expensive. Also, the separate transfer of liquid can lead to contamination of the active pharmaceutical ingredient.

In the publication WO 94/25089, it was therefore proposed that delivery syringes comprising glass receptacles be used for directly storing therein the propofol sensitive to oxygen. However, delivery syringes comprising glass receptacles are not resistant to breakage. As a result, the clamping of such glass receptacles in pump syringe systems is problematic.

It is therefore an object of the present invention to provide an efficient concept for the storage of oxygen-sensitive active pharmaceutical ingredients in receptacles of delivery syringes.

This object is achieved by the features of the independent claims. Advantageous developments are subject matter of the dependent claims, the description and the drawings.

The present invention is based on the insight that the above object can be achieved by using a delivery syringe plastic receptacle which is prefilled with oxygen-sensitive active pharmaceutical ingredient and which is enveloped in an oxygen-tight manner by means of an oxygen-tight envelope. This makes it possible to store oxygen-sensitive active pharmaceutical ingredients in prefilled and oxygen-penetratable plastic receptacles of delivery syringes even over a relatively long period.

The oxygen-tight envelope can, for example in the form of outer packaging or a blister, accommodate the delivery syringe comprising the prefilled plastic receptacle and protect it against the intrusion of oxygen.

According to one aspect, the invention provides a delivery arrangement comprising a delivery syringe comprising a plastic receptacle, wherein the plastic receptacle is filled with an oxygen-sensitive active pharmaceutical ingredient fluid, and an oxygen-tight envelope which envelopes the delivery syringe in an oxygen-tight manner, preferably wherein an inner surface of the plastic receptacle is siliconized at least in sections. This siliconization can in particular increase the sliding capacity of a plunger in the plastic receptacle and additionally protect the active pharmaceutical ingredient fluid.

According to a further aspect, the invention provides a delivery arrangement comprising a delivery syringe comprising a plastic receptacle, wherein the plastic receptacle is filled with an oxygen-sensitive active pharmaceutical ingredient fluid; and an oxygen-tight envelope which envelopes the delivery syringe in an oxygen-tight manner, wherein the oxygen-sensitive active pharmaceutical ingredient fluid is an active pharmaceutical ingredient emulsion and comprises propofol and wherein the plastic receptacle is formed from plastic comprising at least one cyclic olefin copolymer and wherein an inner surface of the plastic receptacle is siliconized at least in sections. Such a plastic receptacle is in particular resistant to propofol acting as solvent. At the same time, the propofol is in particular effectively protected from the oxygen present in the environment.

The oxygen-tight envelope preferably encloses the delivery syringe comprising the filled plastic receptacle, making it possible, even in the case of oxygen-penetratable plastics, to protect the active pharmaceutical ingredient stored in the plastic receptacle against oxygen. The internal space which is enclosed by the envelope and in which the delivery syringe is arranged can be additionally evacuated in order to reduce the oxygen density. However, the internal space enclosed by the envelope can also be filled with a fluid, such as gas or liquid, which is low in oxygen or binds oxygen.

The oxygen-tight envelope has an oxygen transmission rate of less than or equal to 10 $cm^3/m^2$ d bar, preferably of less than or equal to 5 $cm^3/m^2$ d bar, particularly preferably less than or equal to 2 $cm^3/m^2$ d bar. Oxygen transmission rate or oxygen-tightness is determined by the information in the standard DIN 53380.

Moreover, the oxygen-tight envelope also provides a barrier against water vapor. The oxygen-tight envelope has a water vapor transmission rate of less than or equal to 10 $g/m^2$ d, preferably of less than or equal to 5 $g/m^2$ d, particularly preferably less than or equal to 3 $g/m^2$ d. Water vapor transmission rate is determined by the information in the standard DIN 53122.

The plastic receptacle can be completely filled or only partially filled with the active pharmaceutical ingredient fluid.

The delivery syringe can be formed solely by the filled plastic receptacle. In one embodiment, the delivery syringe can comprise a plastic plunger rod. The plastic plunger rod can be a component of the delivery arrangement. However, in one embodiment, the plastic plunger rod is not a component of the delivery arrangement.

In one embodiment, the oxygen-sensitive active pharmaceutical ingredient fluid is an active pharmaceutical ingredient emulsion.

In one embodiment, the active pharmaceutical ingredient fluid comprises an active pharmaceutical ingredient having poor water solubility, with at least 30 ml of water being required to dissolve 1 g of active pharmaceutical ingredient. Therefore, by using the oxygen-tight envelope, it is possible for an entire group of oxygen-sensitive active pharmaceutical ingredients to be stored long-term.

In one embodiment, the active pharmaceutical ingredient fluid is or comprises propofol, more particularly a propofol emulsion. Propofol is described by the chemical name 2,6-diisopropylphenol (IUAPC).

In one embodiment, the plastic receptacle is formed from a cyclic polymer, preferably from a cyclic polyolefin. The plastic receptacle can be formed from plastic comprising one of the following polymers: cyclic olefin copolymer, cyclic olefin polymer or Crystal Clear Polymer. Such a plastic receptacle is resistant to solvents. More particularly, such a plastic receptacle can be used for storing propofol acting as solvent.

In one embodiment, the delivery arrangement or delivery syringe further comprises a plastic plunger rod storable in a shiftable manner in the plastic receptacle, and the plastic plunger rod is in particular arranged beside the plastic receptacle and enveloped in an oxygen-tight manner by means of the oxygen-tight envelope.

In one embodiment, the delivery syringe can basically comprise only the filled plastic receptacle, which is enveloped in an oxygen-tight manner. The plastic plunger rod can then be provided separately. In said embodiment, an oxygen-tight envelope is not required for packaging the plastic plunger rod.

In one embodiment, the plastic plunger rod is formed from plastic comprising one of the following polymers: cyclic olefin copolymer, cyclic olefin polymer or Crystal Clear Polymer, or it is formed from polypropylene.

In a further embodiment of the invention, the plastic receptacle and/or the plastic plunger rod is/are stored in an at least axially shiftable manner in the oxygen-tight envelope. As a result, in the event of a lateral impact, for example axial impact, it is possible for the plastic receptacle and/or the plastic plunger rod to carry out a compensatory movement, for example in the direction of the opposite side, more particularly without themselves being damaged and/or without the shell being damaged. In one embodiment of the invention, the plastic receptacle and/or the plastic plunger rod and the envelope is/are configured such that the two end sides of the plastic receptacle and/or the two end sides of the plastic plunger rod are in each case positionable at a distance from about 0.5 cm to about 2 cm from the inner surface of the envelope. This provides sufficient space to allow an axial compensatory movement.

In a further embodiment of the invention, the plastic receptacle and the plastic plunger rod are stored at least separately by means of at least one flexible spacer, preferably elastic spacer. As a result, impacts in a direction transverse to the longitudinal axis of the plastic receptacle and/or the plastic plunger rod can be absorbed. In one embodiment, the at least one spacer has a width from about 0.3 cm to about 1.5 cm.

In one embodiment, the oxygen-tight envelope comprises an ethylene-vinyl alcohol copolymer barrier, more particularly an ethylene-vinyl alcohol copolymer layer. The presence of the ethylene-vinyl alcohol copolymer barrier makes the envelope oxygen-tight. The ethylene-vinyl alcohol copolymer barrier can, for example, be designed in the form of an ethylene-vinyl alcohol copolymer layer with which the envelope is sealed. However, the ethylene-vinyl alcohol copolymer barrier can be directly provided in plastic from which the oxygen-tight envelope can be produced.

In one embodiment, the oxygen-tight envelope can be constructed from multilayer plastic. The plastic layers can, for example, comprise a polyethylene terephthalate film comprising an ethylene-vinyl alcohol copolymer barrier or polyester comprising an ethylene-vinyl alcohol copolymer barrier. The multilayer plastic can further comprise a peelable polyethylene film, more particularly sealed in an oxygen-tight manner with an ethylene-vinyl alcohol copolymer barrier.

In one embodiment, the oxygen-tight envelope comprises a shell which is formed from thermoplastic, and is more particularly thermoformed. The shell can, for example, be thermoformed in order to accommodate the delivery syringe.

In one embodiment, the shell forms a molding for the formfitting accommodation of the delivery syringe. In this way, the delivery syringe is held in the shell in a formfitting manner. The molding forming the shell can further comprise formfitting accommodation for the plunger rod. The formfitting accommodation in each case can be realized each time by a depression in a shell base. The shell can further be formed such that it is possible to lock the delivery syringe in place therein.

For instance, the shell formed as a molding can, for example, laterally comprise latching projections which are elastic and, upon insertion of the plastic receptacle and/or the plastic plunger rod, are initially displaced and then return to their original position, making it possible to fix the delivery syringe. In one embodiment, the shell has a wall thickness within a range from 50 µm to 5000 µm, preferably from 10 µm to 1000 µm. Measurement is carried out in accordance with DIN 53370.

In one embodiment, the thermoplastic comprises an amorphous polyethylene terephthalate film comprising an ethylene-vinyl alcohol copolymer barrier or biaxially oriented polyester comprising an ethylene-vinyl alcohol copolymer barrier. In one embodiment, the thermoplastic forming the shell has a basis weight within a range from 50 g/m$^2$ to 5000 g/m$^2$, preferably from 300 g/m$^2$ to 1000 g/m$^2$. Measurement is carried out in accordance with ISO 2286-2.

In one embodiment, the shell is sealed in an oxygen-tight manner with a peelable film or polyethylene film or a polyethylene film comprising an ethylene-vinyl alcohol copolymer barrier. In one embodiment, the peelable film has a thickness within a range from 10 µm to 2000 µm, preferably from 50 µm to 300 µm. Measurement is carried out in accordance with DIN 53370. In one embodiment, the peelable film has a basis weight within a range from 10 g/m$^2$ to 1000 g/m$^2$, preferably from 50 g/m$^2$ to 200 g/m$^2$. Measurement is carried out in accordance with ISO 2286-2.

In one embodiment, the oxygen-tight envelope comprises a further shell formed from thermoplastic, more particularly a shell formed from thermoplastic, wherein the further shell comprises an ethylene-vinyl alcohol copolymer barrier, and wherein the further shell is joined, more particularly welded or adhesively bonded, to the shell in an oxygen-tight manner. The further shell can, for example, likewise form a molding for the formfitting accommodation of the delivery syringe. The delivery syringe is therefore held, firstly, by a shell forming a lower part and, secondly, by a lid or by an upper part formed by the further shell. The shell and the further shell are, for example, joined in an oxygen-tight manner along a connecting joint, and this can be realized by welding or adhesive bonding. The shells joined to one another therefore form a stable envelope which can safely accommodate the prefilled plastic receptacle. The further shell can likewise be constructed from plastic and have the same material composition as the shell.

In one embodiment, the plastic receptacle is sealed in a fluid-tight manner at the distal and proximal ends by a detachable closure in each case. The detachable closures can, for example, be designed as plugs or stoppers or plungers or as screw caps. This prevents the active pharmaceutical ingredient fluid from leaking out. The distal-side closure of the plastic receptacle can be formed by a plunger into which it is possible to insert or screw in a plastic plunger rod.

In one embodiment, the delivery arrangement can comprise an oxygen absorber which can, for example, comprise iron powder. The oxygen absorber can be introducible into the shell of the envelope or be joined to the shell.

In one embodiment, the inner surface of the plastic receptacle and/or the outer surface of the plunger and/or the outer surface of the closure is siliconized, more particularly coated with silicone, at least in sections, preferably completely. This increases the sliding capacity thereof. Furthermore, this additionally protects the active pharmaceutical ingredient.

According to a further aspect, the invention provides a method for producing the delivery arrangement according to the invention. The method comprises the steps of providing a delivery syringe comprising a plastic receptacle, of filling the plastic receptacle with an oxygen-sensitive active pharmaceutical ingredient fluid, more particularly with propofol, and of enveloping the delivery syringe comprising the filled plastic receptacle in an oxygen-tight manner by means of an oxygen-tight envelope.

Further features of the production method are directly revealed by the structure of the delivery arrangement according to the invention and by the production steps required in particular for producing the aforementioned plastics.

Figure 2A:
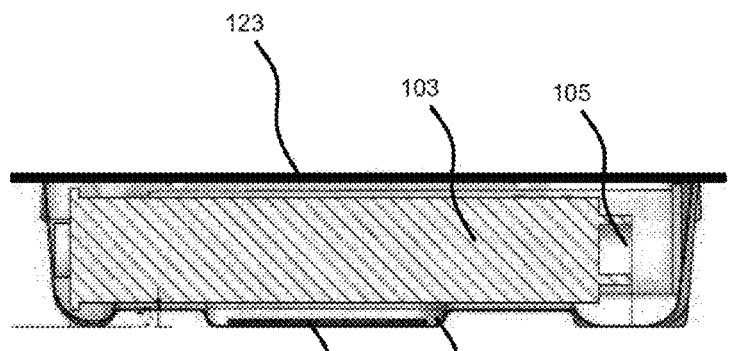

Further embodiments are more particularly elucidated with reference to the attached drawings. What are shown are:

FIG. 1 a diagrammatic view of a delivery arrangement;

FIGS. 2a, b diagrammatic side views of a delivery arrangement; and

Figure 3:
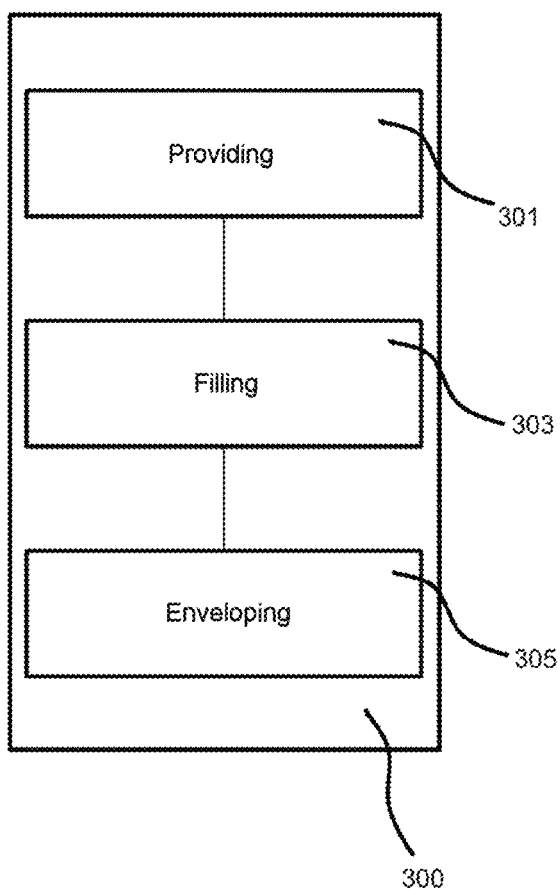

FIG. 3 a flowchart of a production method for producing a delivery arrangement.

FIG. 1 shows diagrammatically a delivery arrangement according to one embodiment. The delivery arrangement comprises a delivery syringe 100 comprising a plastic receptacle 101 and a plastic plunger rod 103. The plunger rod 103 comprises, at the distal end thereof, an insert 105 which is introducible into a plunger 113. Here, for example, the plastic plunger rod 103 is stored outside the plastic receptacle 101.

The plastic receptacle 101 is, as indicated in FIG. 1, filled with an active pharmaceutical ingredient fluid 107, preferably with propofol. The plastic receptacle 101 comprises, at the proximal side, a nozzle 109 which is sealed with a closure 111, for example with a plastic cap. The nozzle 109 has a, preferably male, Luer connector or Luer-Lock connector.

The plastic receptacle 101 is, at the distal side, closed off with a plunger 113 into which it is possible to introduce, for example screw in, the insert 105. In this way, the plastic plunger rod 103 can be completed by the plunger 113. The plunger 113 therefore also simultaneously serves as a distal closure of the plastic receptacle 101. In one embodiment, the plastic plunger rod 103 can already have a plunger instead of the insert 105. In this case, the plunger receptacle 101 is provided at the distal side with a further closure.

Also at the distal side, the plastic receptacle 101 comprises side wings 115, 117 which allow not only manual administration but also use of the delivery syringe in a pump system.

The delivery arrangement further comprises an oxygen-tight envelope 119 which can, for example, be formed as a blister or as packaging and envelopes the delivery syringe 100 completely and in an oxygen-tight manner.

In one embodiment, the oxygen-tight envelope 119 can comprise an oxygen-tight shell 121 and also an oxygen-tight film 123 which seals the shell 121 in an oxygen-tight manner along an edge 125 of the shell 121.

To this end, the shell 121 can be formed from a transparent thermoforming film based on an APET film comprising an EVOH barrier (EVOH: ethylene vinyl alcohol) and a peelable sealing layer composed of polyethylene. The shell 121 is therefore a good oxygen barrier and has high rigidity and also good thermoforming behavior, allowing the shell 121 to be designed as a molding. The shell 121 can have at least one of the following technical properties:

Total thickness: 500 µm, DIN 53370; basis weight: 646 g/m$^2$, ISO 2286-2;

oxygen transmission rate: <1 cm$^3$/m$^2$ d bar, 23° C./35% r.h., DIN 53380;

water vapor transmission rate: <1 g/m$^2$ d, 23° C./85% r.h., DIN 53122.

The film 123 can, for example, be a polyethylene film comprising an EVOH barrier and, as result, likewise be oxygen-tight. The film 123 can further likewise be produced on the basis of an APET film (APET: amorphous polyethylene terephthalate), making it possible to realize an elevated rigidity. The film 123 is, for example, joined along the edge 125 to the shell 121 in an oxygen-tight manner, for example by welding or adhesive bonding.

The shell 121 can be provided as a molding for the formfitting accommodation of the plastic receptacle 101 and the plunger 113. To this end, the shell 121 can comprise an accommodating recess 127 for the accommodation of the plastic receptacle 101 and an accommodating recess 129 for the accommodation of the plastic plunger rod 103.

To hold the plastic receptacle 101, the accommodating recess 127 can comprise clamping projections 131. The accommodating recess 129 can comprise clamping projections 133 to hold the plastic plunger rod 103. The clamping projections 131, 133 are elastic and therefore able to be pushed in upon application of the plastic receptacle 101 and the plastic plunger rod 103, respectively. Owing to the elasticity of the clamping projections 131, 133, they exert a force, for example in a radial direction, on the plastic receptacle 101 and on the plastic plunger rod 103, respectively, making it possible to fix these elements. In one embodiment, the elements 101 and/or 103 can be fixed such that they cannot fall out of the holder, but are at the same time still shiftable in an axial direction. As a result, in the event of an axial impact for example, it is possible for the plastic receptacle 101 and/or the plastic plunger rod 103 to carry out an axial compensatory movement, more particularly without themselves being damaged and/or without the shell 121 being damaged.

The accommodating recess 127 for the accommodation of the plastic receptacle 101 and the accommodating recess 129 for the accommodation of the plastic plunger rod 103 are arranged separately by means of at least one spacer 130. In the embodiment shown, they are arranged separately by means of two spacers 130. Arranged on the spacers 130 are the aforementioned clamping projections 131, 133. The spacers 130 are flexible, preferably elastic. As a result, impacts in a direction transverse to the longitudinal axis of the plastic receptacle 101 and/or the plastic plunger rod 103 can be cushioned. The two spacers 130 are each provided by a type of wall section.

In one embodiment, the shell 121 and/or the film 123 can be formed from a plastic composite composed of biaxially oriented polyester comprising a coextruded sealing barrier layer composed of polyethylene, EVOH, polyethylene. Such a plastic composite is notable for good transparency. Furthermore, it is possible to realize a broad sealing area and a good oxygen barrier. A film 123 formed in this manner can be used in particular as a lid film for sealing thermoformed shells, for example the shell 121. The film 123 can have at least one of the following technical properties:

total thickness: 100 μm, DIN 53370; basis weight: 107.5 g/m$^2$, ISO 2286-2; longitudinal tensile strength: 40-60 N/mm$^2$, ISO 527-3; transverse tensile strength: 35-55 N/mm$^2$, ISO 527-3; longitudinal elongation at break: 40-120%, ISO 527-3; transverse elongation at break: 40-120%, ISO 527-3; oxygen transmission rate: 1 cm$^3$/m$^2$ d bar, 23° C./35% r.h., DIN 53380; $CO_2$ transmission rate: <4 cm$^3$/m$^2$ d bar, 23° C./35% r.h., DIN 53380; $N_2$ transmission rate: <1 cm$^3$/m$^2$ d bar, 23° C./35% r.h., DIN 53380.

In one embodiment, the plastic receptacle 101 is formed from a cyclic polymer. Cyclic polymers have a high purity and also a resistance, ensuring a relatively long storage of active pharmaceutical ingredients. However, cyclic polymers are oxygen-penetrable or oxygen-permeable. This oxygen permeability is disadvantageous not only for oxygen-sensitive products, such as oil-in-water emulsions, but also for oxygen-sensitive active pharmaceutical ingredients, such as propofol.

In one embodiment, this oxygen permeability of the plastic receptacle 101 is compensated for by providing the envelope 119, which can be constructed from a plastic blister and can have a barrier layer with respect to oxygen.

In one embodiment, the plastic receptacle 101 is formed from COC (cyclic olefin copolymer), COP (cyclic olefin polymer) or CCP (Crystal Clear Polymer). These have been found to be resistant to propofol acting as solvent. The plunger 113 and/or the closure 111 is, for example, formed from rubber, more particularly from bromobutyl. The plastic plunger rod 103 can, for example, be formed from polypropylene.

In one embodiment, the plastic receptacle 101 can be a transparent plastic selected from the group of cyclic olefin copolymers or cyclic olefin polymers. The envelope 119 forms an oxygen-impenetrable packaging which encloses the plastic receptacle 101 filled with the active pharmaceutical ingredient fluid 107.

In one embodiment, the inner surface of the plastic receptacle 101 is siliconized or coated with silicone. This increases the sliding capacity thereof. Furthermore, this additionally protects the active pharmaceutical ingredient.

In a further embodiment, plunger 113 is siliconized at least in sections. In one embodiment, the closure 11 is also siliconized at least in sections.

Figure 2B:
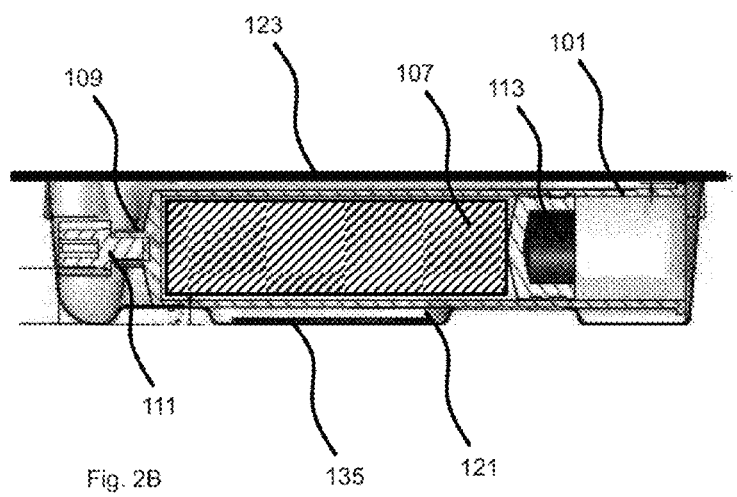

FIGS. 2a and 2b show different side views of the delivery arrangement shown in FIG. 1. In one embodiment, the delivery arrangement can comprise a nonfluidic oxygen absorber 135, which can, for example, comprise iron dust. The oxygen absorber 135 is, for example, arranged at the base of the shell 121.

FIG. 3 shows a chart of a method for producing a delivery arrangement. The method 300 comprises step 301 of providing a delivery syringe comprising a plastic receptacle, step 303 of filling the plastic receptacle with an oxygen-sensitive active pharmaceutical ingredient fluid, for example with propofol or with a propofol fluid, more particularly a propofol emulsion, and oxygen-tight enveloping 305 of the delivery syringe comprising the filled plastic receptacle by means of an oxygen-tight envelope. The method further comprises the step of arranging the prefilled plastic receptacle 101 and the plastic plunger rod 103 in the thermoformed shell 121 and also the oxygen-tight sealing of the shell 121 with the lid film 123 by means of, for example, welding or adhesive bonding.

In one embodiment, an advantage of the delivery arrangement is the ease of use thereof without the need to transfer an active pharmaceutical ingredient to further containers. Furthermore, the delivery syringe can be directly removed and used without the need for further assembly steps. The plastic receptacle 101 has, for example, a capacity of 50 ml, making it possible for the plastic receptacle to be automatically recognized by conventional pump systems. The use of the plastic receptacle achieves a resistance to breakage that is increased with respect to glass. Furthermore, waste quantity can be reduced coupled with simultaneous time savings as a result of elimination of administration preparation steps, which are, for example, caused by transfer of the active pharmaceutical ingredient.

LIST OF REFERENCE SIGNS

100 Delivery syringe
101 Plastic receptacle
103 Plastic plunger rod
105 Insert
107 Active pharmaceutical ingredient fluid
109 Nozzle
111 Closure
113 Plastic plunger
115 Side wing
117 Side wing
119 Oxygen-tight envelope
121 Shell
123 Film
125 Edge
127 Accommodating recess for the delivery syringe
129 Accommodating recess for the plunger rod
130 Spacer or wall section between the accommodating recess for the delivery syringe and the accommodating recess for the plunger rod
131 Clamping projection
133 Clamping projection
135 Oxygen absorber
300 Method
301 Providing step
303 Filling step
305 Oxygen-tight enveloping

The invention claimed is:

1. A delivery arrangement comprising:
a delivery syringe comprising a transparent plastic receptacle, wherein the plastic receptacle is filled with an oxygen-sensitive active pharmaceutical ingredient fluid and wherein the oxygen-sensitive active pharmaceutical ingredient fluid is an active pharmaceutical ingredient emulsion;
a transparent oxygen-tight envelope which envelopes the delivery syringe in an oxygen-tight manner and comprises an ethylene-vinyl alcohol copolymer barrier wherein the oxygen-tight envelope is filled with a fluid which is low in oxygen or binds oxygen;
an oxygen absorber which is placed in the oxygen-tight envelope;
wherein the plastic receptacle is formed from plastic comprising at least one of the following polymers: cyclic olefin copolymer, cyclic olefin polymer or Crystal Clear Polymer and an inner surface of the plastic receptacle is siliconized at least in sections.

2. The delivery arrangement as claimed in claim 1, wherein the active pharmaceutical ingredient fluid comprises an active pharmaceutical ingredient having a water solubility in which at least 30 ml of water are required to dissolve 1 g of active pharmaceutical ingredient.

3. The delivery arrangement as claimed in claim 1, wherein the active pharmaceutical ingredient fluid comprises propofol.

4. The delivery arrangement as claimed in claim 1, wherein the delivery syringe comprises a plastic plunger rod storable in a shiftable manner in the plastic receptacle more particularly a plastic plunger rod which is storable in a shiftable manner in the plastic receptacle and arranged beside the plastic receptacle and which is enveloped in an oxygen-tight manner by means of the oxygen-tight envelope.

5. The delivery arrangement as claimed in claim 4, wherein the plastic plunger rod is formed from plastic comprising at least one of the following polymers: cyclic olefin copolymer, cyclic olefin polymer or Crystal Clear Polymer, or is formed from polypropylene.

6. The delivery arrangement as claimed in claim 1, wherein the plastic receptacle and/or the plastic plunger rod is/are stored in an at least axially shiftable manner in the oxygen-tight envelope.

7. The delivery arrangement as claimed in claim 1, wherein the plastic receptacle and/or the plastic plunger rod are stored at least separately by means of at least one flexible spacer.

8. The delivery arrangement as claimed in claim 1, wherein the oxygen-tight envelope comprises an ethylene-vinyl alcohol copolymer layer.

9. The delivery arrangement as claimed in claim 1, wherein the oxygen-tight envelope comprises a shell which is formed from thermoplastic being thermoformed.

10. The delivery arrangement as claimed in claim 9, wherein the thermoplastic comprises an amorphous polyethylene terephthalate film comprising an ethylene-vinyl alcohol copolymer barrier or biaxially oriented polyester comprising an ethylene-vinyl alcohol copolymer barrier.

11. The delivery arrangement as claimed in claim 9, wherein the shell is sealed in an oxygen-tight manner with a peelable polyethylene film or a polyethylene film comprising an ethylene-vinyl alcohol copolymer barrier.

12. The delivery arrangement as claimed in claim 9, wherein the oxygen-tight envelope comprises a film including an ethylene-vinyl alcohol copolymer barrier, and wherein the film is welded or adhesively bonded, to the shell in an oxygen-tight manner.

13. The delivery arrangement as claimed in claim 9, wherein the plastic receptacle is sealed in a fluid-tight manner at the distal and proximal ends by a detachable closure in each case.

14. A delivery arrangement comprising:
a delivery syringe comprising a transparent plastic receptacle, wherein the plastic receptacle is filled with an oxygen-sensitive active pharmaceutical ingredient fluid; and
a transparent oxygen-tight envelope which envelopes the delivery syringe in an oxygen-tight manner and comprises an ethylene-vinyl alcohol copolymer barrier,
wherein the oxygen-sensitive active pharmaceutical ingredient fluid is an active pharmaceutical ingredient emulsion and comprises propofol and
wherein the plastic receptacle is formed from plastic comprising at least one of the following polymers: cyclic olefin copolymer, cyclic olefin polymer or Crystal Clear Polymer and
wherein an inner surface of the plastic receptacle is siliconized at least in sections.

15. The delivery arrangement as claimed in claim 1, wherein the oxygen-tight envelope comprises a shell which forms a molding for the formfitting accommodation of the delivery syringe.

16. A delivery arrangement comprising:
a delivery syringe comprising a transparent plastic receptacle,
wherein the plastic receptacle is filled with an oxygen-sensitive active pharmaceutical ingredient fluid and wherein the oxygen-sensitive active pharmaceutical ingredient fluid is an active pharmaceutical ingredient emulsion;
an oxygen-tight envelope which envelopes the delivery syringe in an oxygen-tight manner wherein the oxygen-tight envelope is filled with a fluid which is low in oxygen or binds oxygen;
an oxygen absorber which is placed in the oxygen-tight envelope;
wherein the plastic receptacle is formed from plastic comprising at least one of the following polymers: cyclic olefin copolymer, cyclic olefin polymer or Crystal Clear Polymer and an inner surface of the plastic receptacle is siliconized at least in sections and
wherein the oxygen-tight envelope comprises a transparent shell which is formed from thermoplastic being thermoformed and the thermoplastic comprises an amorphous polyethylene terephthalate film comprising an ethylene-vinyl alcohol copolymer barrier;
wherein the oxygen-tight envelope has an oxygen transmission rate of less than or equal to 5 $cm^3/m^2$ d bar and a water vapor transmission rate of less than or equal to 5 $g/m^2$ d.

* * * * *